United States Patent
Johansson et al.

(10) Patent No.: US 9,259,361 B2
(45) Date of Patent: Feb. 16, 2016

(54) ABSORBENT ARTICLE

(71) Applicant: SCA Hygiene Products AB, Göteborg (SE)

(72) Inventors: Charlotte Johansson, Göteborg (SE); Susanne Fredrikson, Mölndal (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 0 days.

(21) Appl. No.: 14/406,376

(22) PCT Filed: Jun. 5, 2013

(86) PCT No.: PCT/EP2013/061571
§ 371 (c)(1),
(2) Date: Dec. 8, 2014

(87) PCT Pub. No.: WO2013/186098
PCT Pub. Date: Dec. 19, 2013

(65) Prior Publication Data
US 2015/0148769 A1 May 28, 2015

(30) Foreign Application Priority Data

Jun. 11, 2012 (WO) .................. PCT/EP2012/061010

(51) Int. Cl.
*A61F 13/15* (2006.01)
*A61F 13/475* (2006.01)
(Continued)

(52) U.S. Cl.
CPC ....... *A61F 13/4756* (2013.01); *A61F 13/15203* (2013.01); *A61F 13/47* (2013.01);
(Continued)

(58) Field of Classification Search
CPC ................ A61F 13/47; A61F 13/4704; A61F 13/47236; A61F 13/47245; A61F 13/4751; A61F 13/4752; A61F 13/49413; A61F 13/495; A61F 13/535; A61F 2013/4706; A61F 2013/47281; A61F 2013/49493; A61F 2013/5355
See application file for complete search history.

(56) References Cited

U.S. PATENT DOCUMENTS 4,988,344 A 1/1991 Reising et al.
5,062,840 A * 11/1991 Holt et al. ................ 604/385.19
(Continued)

FOREIGN PATENT DOCUMENTS

EP 0 343 941 A2 11/1989
JP 2003-144491 A 5/2003
(Continued)

OTHER PUBLICATIONS

International Search Report (PCT/ISA/210) mailed on Aug. 29, 2013, by the European Patent Office as the International Searching Authority for International Application No. PCT/EP2013/061571.
(Continued)

*Primary Examiner* — Lynne Anderson
(74) *Attorney, Agent, or Firm* — Buchanan Ingersoll & Rooney PC

(57) ABSTRACT

An absorbent article has longitudinal side edges, transversal end edges, and an absorbent core. The absorbent core comprises a first absorbent layer having an opening and a fluid flow control structure between said first absorbent layer and a backsheet. An elastic member is arranged along each longitudinal side edge. The first absorbent layer has a longitudinal front portion, a longitudinal back portion and a narrow transversal transition located between said front and back portions. The width of the narrow transversal transition is 50-75% of the widest transversal width of the front portion, and 20-50% of the longitudinal length of the opening is located in the front portion. The front portion constitutes 20-40% of the total longitudinal length of the first absorbent layer. An interspace is located in an area between the elastic member and the first absorbent layer at least in an area laterally outside the narrow transversal transition.

16 Claims, 3 Drawing Sheets

(51) Int. Cl.
*A61F 13/47* (2006.01)
*A61F 13/535* (2006.01)
*A61F 13/537* (2006.01)
*A61F 13/511* (2006.01)
*A61F 13/514* (2006.01)
*A61F 13/472* (2006.01)

(52) U.S. Cl.
CPC ......... *A61F13/4751* (2013.01); *A61F 13/4752* (2013.01); *A61F 13/4757* (2013.01); *A61F 13/47245* (2013.01); *A61F 13/511* (2013.01); *A61F 13/514* (2013.01); *A61F 13/535* (2013.01); *A61F 13/53756* (2013.01); *A61F 2013/15357* (2013.01); *A61F 2013/15365* (2013.01); *A61F 2013/47281* (2013.01)

(56) References Cited

U.S. PATENT DOCUMENTS

| | | | | |
|---|---|---|---|---|
| 5,134,007 | A * | 7/1992 | Reising et al. | 428/78 |
| 5,176,672 | A * | 1/1993 | Bruemmer et al. | 604/385.19 |
| 6,192,262 | B1 | 2/2001 | Godik | |
| 6,293,933 | B1 * | 9/2001 | Ahlstrand | 604/385.101 |
| 2003/0130643 | A1 | 7/2003 | Drevik et al. | |
| 2010/0256586 | A1 | 10/2010 | Bergström et al. | |
| 2010/0331804 | A1 | 12/2010 | Larsson | |
| 2013/0231628 | A1 * | 9/2013 | Dieringer et al. | 604/385.101 |
| 2015/0173971 | A1 * | 6/2015 | Johansson et al. | 604/385.101 |

FOREIGN PATENT DOCUMENTS

| | | |
|---|---|---|
| WO | WO 91/09582 A1 | 7/1991 |
| WO | WO 01/05304 A1 | 1/2001 |
| WO | WO 2009/067059 A1 | 5/2009 |

OTHER PUBLICATIONS

Written Opinion (PCT/ISA/237) mailed on Aug. 29, 2013, by the European Patent Office as the International Searching Authority for International Application No. PCT/EP2013/061571.

International Search Report (PCT/ISA/210) mailed on Feb. 7, 2013, by the European Patent Office as the International Searching Authority for International Application No. PCT/EP2012/061010.

Written Opinion (PCT/ISA/237) mailed on Feb. 7, 2013, by the European Patent Office as the International Searching Authority for International Application No. PCT/EP2012/061010.

* cited by examiner

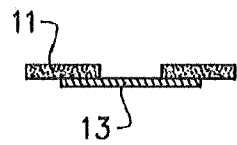
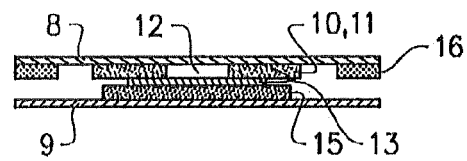
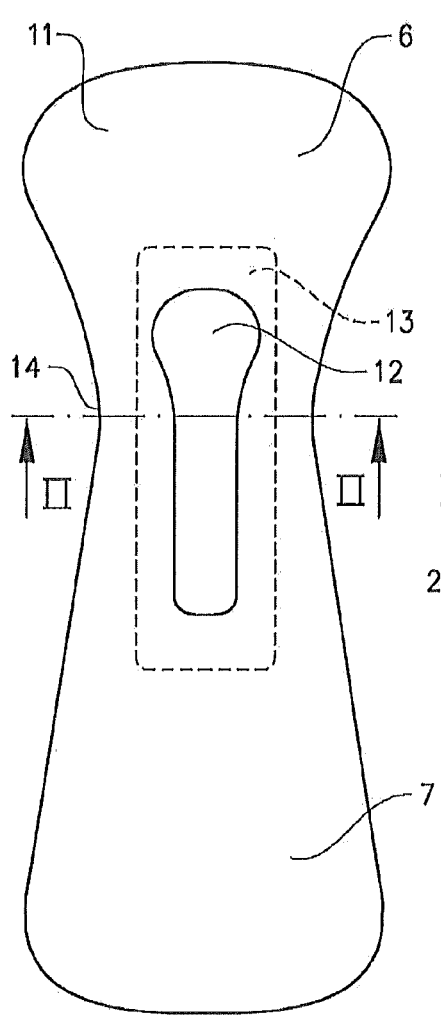
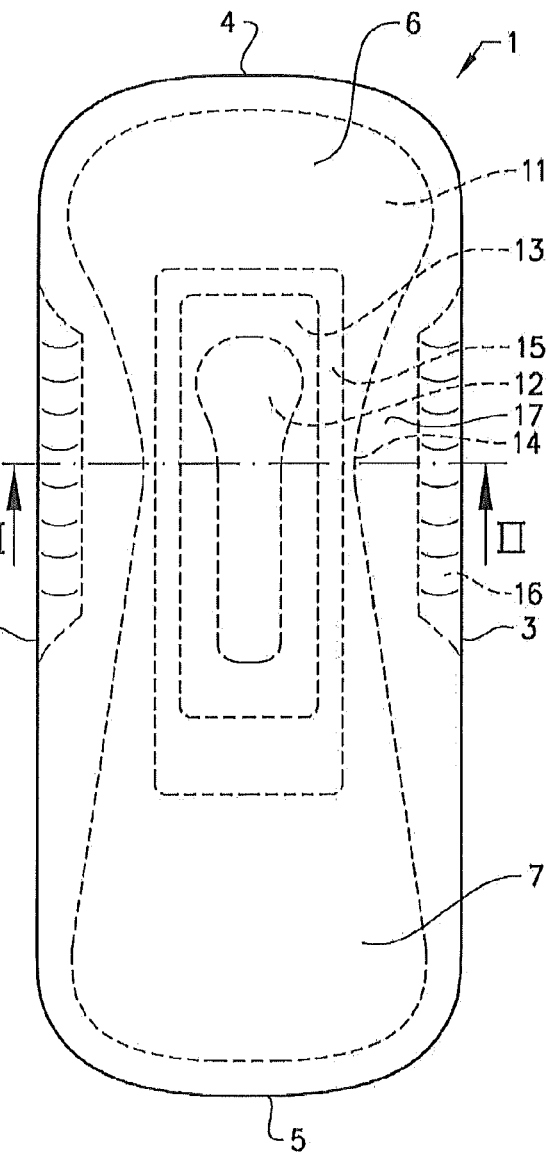

ABSORBENT ARTICLE

TECHNICAL FIELD

The present disclosure concerns an absorbent article such as a sanitary napkin or incontinence pad comprising an absorbent core having an opening extending there through.

BACKGROUND

Absorbent articles of the kind that is worn inside ordinary underpants include absorbent napkins or pads for adult incontinence or feminine use.

The napkins or pads are generally provided with an absorbent core to receive and retain body liquids. In order for such absorbent articles to function efficiently, the absorbent core should quickly acquire body liquids into the structure from the point of application and subsequently distribute the body liquids within and throughout the absorbent core to provide maximum leakage containment. An acquisition/distribution layer in connection to the core and an opening of the core aids when subsequent insults are directed to the same local area as previous insults, as the local area tends to be already filled with liquid from the previous insult.

As these types of articles have to be sized and configured to fit in the limited space available in the crotch portion of the underwear, a particular problem is that they may leak at the side edges, before the full absorption capacity of the article has been utilized. The fluid will instead flow on the topsheet and out over the side edges of the article where it can leak out and soil the wearer's clothing. A further drawback when fluid flows on the outside of the topsheet is that a large portion of the body-contacting topsheet will be wet. This is of course highly undesirable as it makes the article unhygienic and unpleasant to wear.

Great efforts have been made in the past in order to overcome the side leakage problem in relation to napkins and pads for incontinence or feminine use.

WO 2009067059 A1 discloses an absorbent article comprising an absorbent core having fold indications and a forming element in order to obtain a double-bowl shape of the article. Although prior art designs may alleviate the side leakage problem to some extent, there is still a great need for further improvements of the side leakage security for the kind of absorbent article that is worn in the crotch portion of an undergarment.

SUMMARY

It is an object of the present disclosure to provide an improved solution that alleviates the mentioned drawback with present articles.

The present disclosure concerns an absorbent article according to claim 1 having a new and improved shape in the form of a scoop-shaped article leading to an improved side-leakage security. Such a scoop-shaped article has an improved body-fit along the whole length of the article. The article has a curved front portion in order to follow the curvature of the crotch of the wearer and a substantially non-curved back portion to allow for a close contact with the buttocks of the wearer.

Thus, an absorbent article in a form of a sanitary napkin or incontinence pad according to the present disclosure has longitudinal side edges and transversal end edges and comprises a fluid permeable topsheet, a fluid impermeable backsheet and an absorbent core located between the topsheet and the backsheet. The absorbent core comprises a first absorbent layer having a longitudinal front portion and a longitudinal back portion, the first absorbent layer having an opening extending there through and 20-50% of the longitudinal length of the opening located in the front portion of the first absorbent layer. A fluid flow control structure is located between the first absorbent layer and the backsheet, and an elastic member is arranged along each longitudinal side edge of the absorbent article. A narrow transversal transition is located between the front portion and the back portion of the first absorbent layer. The width of the narrow transversal transition is 50-75% of the widest transversal width of the front portion of the first absorbent layer. The front portion of the first absorbent layer constitutes 20-40% of the total longitudinal length of the first absorbent layer. An interspace is located in an area between the elastic member and the first absorbent layer, at least in an area laterally outside the narrow transversal transition.

The interspace may be substantially free from absorbent material, which means herein that it is free from any intentionally added absorbent material, but may include spill from the production process.

The interspace may have a maximum lateral extension between an inner side edge of the elastic member and a proximal side edge of the first absorbent layer of at least 15 mm and less than 40 mm in order for the front part and the back part of the first absorbent layer to be able to form a substantially right-angled relationship, such an angle may be 45-90°.

The front portion of the first absorbent layer constitutes 20-40% of the total longitudinal length of the first absorbent layer. An asymmetric shape of the article resulting from a shorter longitudinal length of the front portion of the first absorbent layer in relation to the back portion and a narrow transversal transition there between further improves the fit of the article in the crotch of the wearer and the leakage security of the article. A concurrent larger longitudinal back portion of the article further provides a high capacity and leakage security at the rear of the article, located in the area of the buttocks of the wearer.

The elastic members are arranged along each longitudinal side edge of the sanitary napkin, at least they may be arranged laterally outside the narrow transversal transition between the front portion and the back portion of the first absorbent layer. The longitudinal extension of the hole and the elastic members in the back portion of the first absorbent layer may be 20-50%. The maximal longitudinal extension of the elastic member in the back portion of the first absorbent layer may substantially be the longitudinal extension of the opening in the back portion of the first absorbent layer, in order to obtain an enhanced scoop shape of the article.

As used herein the term "scoop-shape" refers to the general shape of the absorbent article of the present disclosure and as exemplified in FIG. 6. This may entail an article having a front part and a back part having an angled relationship, such as 45-90°. The front part of the article may have an angled or a substantially half cup-shape and the back portion of the article may have a substantially flat shape. The combination of the interspace, the elastic members and the specific asymmetric shape of the first absorbent layer aids in providing the characteristic scoop shape of the article leading to an improved fit of the article on the wearer and thereby a reduced side leakage.

The width of the narrow transversal transition may be 55-70% of the widest transversal width of the front portion of the first absorbent layer in order to obtain an improved hook behind the tendons of the wearer. The width of the narrow transversal transition may be 50-75% or 55-70% of the widest transversal width of the back portion of the first absorbent layer in order to ensure an improved fit of the article. The widest transversal width of the front portion and the back portion may be about 75-170 mm. The longitudinal extension of the narrow transversal transition may be 5-20% of the longitudinal length of the first absorbent layer to further ensure that the article has a proper fit and stays in place during use. The width of the narrow transversal transition of the first absorbent layer may be less than 130 mm and larger than 30 mm, or less than 90 mm and larger than 50 mm for an improved fit of the article between the tendons of the wearer. The longitudinal length of the first absorbent layer may be about 230-400 mm.

The first absorbent layer has at least one opening extending completely through the layer, thereby forming a cavity in the article. 20-50% or 20-40% of the longitudinal length of the opening may be located in the front portion of the first absorbent layer in order to ensure a proper placement of the hole in relation to the wetting point of the article. The longitudinal length of the opening in the first absorbent layer may be 20-40% of the longitudinal length of the first absorbent layer in order to ensure fluid flow into the opening and not on the outside of the topsheet. The transverse dimension of the opening may be larger in the front portion of the first absorbent layer than the transverse dimension of the opening in the back portion of the first absorbent layer in order to improve the fluid intake rate through the hole and further into the fluid flow control structure. The first absorbent layer may have one opening only for both leakage security and improved feeling of safety for the user.

A second absorbent layer may be located between the fluid flow control structure and the backsheet in order to further increase the absorption capacity of the article. The second absorbent layer may have a smaller surface area than the first absorbent layer in order to enhance the scoop-shape of the article. The first absorbent layer may extend further forward and rearward in the absorbent article than the second absorbent layer. The article may comprise one or more further absorbent layers.

The fluid flow control member is arranged between the first absorbent layer and the backsheet, but may also be arranged between the first absorbent layer and a second absorbent layer. The first absorbent layer may be placed beneath and in direct contact with the topsheet, or may alternatively be placed in indirect contact with the topsheet through one or more intervening components such as tissue layers, acquisition layers or further absorbent layers. Similarly, the second absorbent layer may be placed directly beneath the fluid flow control member and in direct contact with the fluid flow control member and the backsheet, or may be in indirect contact with one or both of those components by intervening components. By arranging the fluid flow control member between the first and second absorbent layers, it forms a channel in the absorbent article and leads the fluid to the back and front of the article. The contact area between the fluid flow control member and the absorbent core increases which facilitates distribution and rapid absorption of liquid in the article.

The absorbent article is in the form of an incontinence pad or a sanitary napkin, and may be for feminine or incontinence use, and may have an elongate, generally rectangular shape when fully extended in all directions. In this context, a generally rectangular shape is intended to encompass also that, for instance, the corners of the absorbent article may be rounded, or that the edges of the absorbent article may not be completely linear. The absorbent article may have two longitudinal side edges having equal length and extending generally in the same direction.

The topsheet and the backsheet of the absorbent article may extend together laterally outside the first absorbent layer along the whole circumference of the article and be connected to each other in an edge joint around the periphery of the absorbent core for leakage security. The topsheet may cover part of the backsheet to form an edge barrier.

The topsheet may consist of any material which is suitable for the purpose, i.e. be soft and liquid pervious. Examples of topsheet materials are nonwoven materials, perforated plastic films, plastic or textile mesh, and fluid permeable foam layers. Laminates consisting of two or more topsheet materials may also be employed, as are top sheets consisting of different materials within different parts of the fluid permeable wearer-facing surface.

The backsheet is fluid impermeable. However, backsheet materials that are only fluid repellant may be used particularly in instances where relatively small amounts of urine are expected to be taken up. The backsheet may be a thin, flexible, fluid-impermeable plastic film, such as of polyethylene or polypropylene, but fluid-impermeable nonwoven materials, fluid impermeable foams and fluid impermeable laminates are also contemplated within the scope of the present disclosure. The backsheet may be breathable, implying that air and vapor may pass through the backsheet. Furthermore, the backsheet may have an outer, garment-facing surface of a textile material such as nonwoven.

The absorbent core comprises a first absorbent layer. It may comprise one absorbent layer only, but may comprise a second or further absorbent layer. The absorbent core may be made up of any suitable absorbent or fluid uptake material, such as one or more layers of cellulose fluff pulp, foam, highloft, etc. The absorbent core may contain fibers or particles of highly absorbent polymer material, commonly known as superabsorbents, which are materials having the ability to absorb and retain large quantities of fluid upon formation of a hydrogel. The superabsorbent may be mixed with cellulose fluff pulp and/or may be arranged in pockets or layers in the absorbent core. The fibers may be pulp fibers and the superabsorbent material may be polyacrylate-based particles. The absorbent structure may comprise 40-80% superabsorbent and 60-20% pulp fibers. The absorbent core may further incorporate components for improving the properties of the absorbent core. Some examples of such components are binder fibers, fluid-dispersing materials, wetness indicators, fluid acquisition materials, etc.

The absorbent layers may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may comprise a mixture of absorbent and/or non-absorbent fibers and superabsorbent material, wherein the ratio of superabsorbent material to fibers may vary in the layer. One or more compressed lines, acting as hinges, may advantageously be arranged in the first absorbent layer, which may be relatively stiff, to facilitate folding of the absorbent article.

The topsheet may extend down into the cavity that is defined by the opening in the first absorbent layer and the surface of the fluid flow control structure that is facing the topsheet. Thereby, the cavity will be lined with topsheet material and will be accessible from the outer body facing surface of the absorbent article. A part of the fluid that is collected in the cavity may be absorbed by the first absorbent layer through the walls of the cavity. However, the major part of the fluid will continue downward in the absorbent article, through the bottom of the cavity and into the fluid flow control member where it is distributed longitudinally and laterally along the flow control member.

The fluid flow control member may be of rectangular shape and may be surrounded in the longitudinal and lateral directions by portions of the absorbent core. Other shapes and configurations for the fluid flow control structure may also be used. However, it is generally advantageous if the fluid flow control member has smaller width and is shorter than the absorbent core, as this facilitates distribution to a large area of the absorbent core.

Elastic members are arranged along each longitudinal side edge of the sanitary napkin, at least they may be arranged laterally outside the narrow transversal transition between the front portion and the back portion of the first absorbent layer, to further improve the shape of the article. The elastic members are may be located there between the topsheet and the backsheet. The absorbent article may have an interspace, located along each side edge of the first absorbent layer, substantially free from absorbent material in order to obtain the specific shape according to the present disclosure leading to an improved fit of the article on the wearer. The interspace may be located adjacent the narrow transversal transition of the first absorbent layer in an area between the elastics, located at the periphery of the article, and the periphery of the first absorbent layer.

The absorbent article may further include fastening means for fastening of the absorbent article inside a supporting pant garment, such as a pair of underpants. The fastening means may be covered by a releasable protective layer.

BRIEF DESCRIPTION OF THE DRAWINGS

Embodiments will be more closely described with reference to the enclosed Figures, in which:

FIG. 1 is a plan view of the first absorbent layer and the fluid flow control structure of an absorbent article according to the invention.

FIG. 2 is a cross-sectional view along the line II-II in FIG. 1.

FIG. 3 is a plan view of an embodiment of an absorbent article according to the invention.

FIG. 4 is a cross-sectional view along the line II-II in FIG. 3.

DETAILED DESCRIPTION OF DRAWINGS

Figure 5:
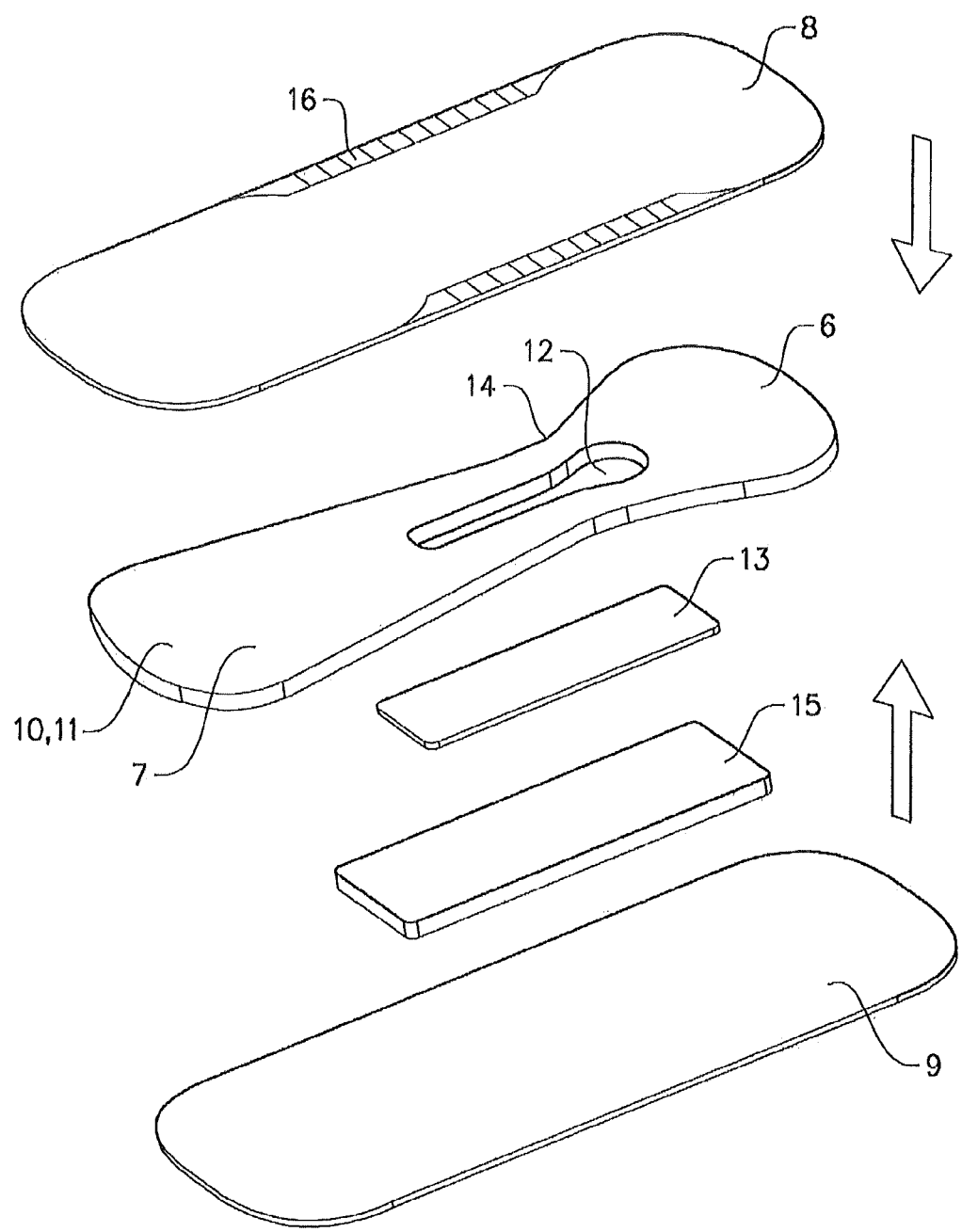
FIG. 5 is an exploded 3-D view of the absorbent article of FIG. 3.

The present disclosure will be described more closely below by an exemplary embodiment. The present disclosure may however be embodied in many different forms and should not be construed as limited to the embodiments set forth in the drawings and the description thereto.

FIG. 3 schematically discloses an absorbent article 1 in the form of an incontinence pad seen from the side that is intended to be facing towards a wearer's body when the article 1 is being worn. The article 1 has two longitudinal side edges 2, 3 having equal length and extending generally in the same direction. Front and rear end edges 4, 5 extend transversely at the ends of the article 1. The rear end edge 5 is intended to be orientated rearwards during use of the article 1, and the front end edge 4 is intended to be facing forwards towards the abdomen of the wearer. The article 1 comprises a fluid permeable topsheet 8, a fluid impermeable backsheet 9 and an absorbent core 10 having a first absorbent layer 11 and a fluid flow control structure 13, enclosed between the topsheet 8 and the backsheet 9 as seen in FIG. 4. The core in FIGS. 3-5 comprises a second absorbent layer 15 located between the fluid flow control structure 13 and the backsheet 9. The topsheet 8 and the backsheet 9 of the article 1 are shown to extend together laterally outside of the first absorbent layer 11 along the whole circumference and are connected to each other in an edge join around the periphery of the article 1. The edge joint may be formed in any suitable manner as known in the art such as by means of adhesive, ultrasonic bonding, thermo-bonding, stitching, etc. The topsheet 8 and the backsheet 9 may consist of any material suitable, such as a non-woven or film material, for the particular purpose, as disclosed herein.

Elastic members 16, such as a band of elastic material, e.g. foam elastics, are arranged between the topsheet 8 and the backsheet 9 and along the longitudinal side edges of the first absorbent layer 1. The elastics are located in the area outside the narrow transversal transition 14, which is located between the front part 6 and the back part 7 of the first absorbent layer 11. An interspace 17 is located in an area between the elastic member 16 and the narrow transversal transition 14, i.e. laterally outside the narrow transversal transition of the first absorbent layer 11. The interspace 17 is substantially free from absorbent material. The interspace 17, the elastic members 16 and the specific asymmetric shape of the first absorbent layer 11 enables the characteristic scoop shape of the article and improves the fit of the article on the wearer leading to reduced side leakage. The elastic members 16 are thus consistently arranged to contribute to an angle between the front portion 6 and the back portion 7 of the first absorbent layer 11 of 45-90°.

FIGS. 1 and 2 show a first absorbent layer 11 having an opening 12 extending there through. A fluid flow control structure 13 is located beneath the first absorbent layer 11. The first absorbent layer 11 has a longitudinal front portion 6 and a longitudinal back portion 7 and a narrow transversal transition 14 located between the front portion 6 and the back portion 7 as seen in FIG. 1. The width of the narrow transversal transition 14 is 50-75% of the widest transversal width of the front portion 6 of the first absorbent layer 11 and 50-75% of the widest transversal width of the back portion 7 of the first absorbent layer, such as 65 mm. The widest transversal width of the front portion 6 and the back portion 7 may be about 75-170 mm, such as 100 mm. The longitudinal extension of the narrow transversal transition 14 is 5-20% of the longitudinal length of the first absorbent layer 11. The front portion of the first absorbent layer is 20-40% of the longitudinal length of the first absorbent layer. The longitudinal length of the first absorbent layer 11 may be about 230-400 mm, such as 300 mm.

The absorbent article 1 as shown in FIG. 3 has an elongate, generally rectangular shape when fully extended in all directions. The word "generally" in this context means that, for instance, the corners of the incontinence protector 1 may be rounded, or the edges of the incontinence protector 1 may not be completely linear.

The absorbent article 1 may further have fastening means (not shown in the figures) for fastening of the article 1 inside a supporting pant garment, such as a pair of underpants. The fastening means may be in the form of two longitudinally extending bands of pressure sensitive adhesive arranged on the garment-facing surface of the backsheet 9. The fastening means may be covered by a releasable protective layer. The protective layer may be a siliconized paper, a nonwoven or any other releasable material as is known in the art. Before placing the incontinence protector in the supporting pant garment, the protective layer is removed from the fastening means to expose the adhesive and make it available for fastening to the pant garment.

The fastening means is optional and may be omitted, if desired. When using an adhesive fastening means, any suitable adhesive pattern may be used such as full coating of the backsheet, one or more longitudinal adhesive band, transverse bands, dots, circles, curves, stars, etc. Furthermore, the fastening means may be a mechanical fastener such as hook-type fasteners, clips, press studs, etc. or may be a frictional fastener such as a frictional coating or open-celled foam. Combinations of different types of fasteners are also conceivable.

The absorbent core 10 of the absorbent article 1 shown in FIG. 3 comprises a first absorbent layer 11 and a second absorbent layer 15. The absorbent layers may comprise a mixture of absorbent and/or non-absorbent fibers and superabsorbent material. A fluid flow control structure 13 is arranged between the first absorbent layer 11 and the second absorbent layer 15. In the absorbent article 1 in FIG. 3 the first absorbent layer 11 is placed beneath and in direct contact with the topsheet 8.

The second absorbent layer 15 is shown to have a generally rectangular shape. The second absorbent layer 15 is placed beneath the first absorbent layer 11. The second absorbent layer 15 is somewhat smaller than the first absorbent layer 11 so that the first absorbent layer 11 extends beyond the second absorbent layer 15 forward and rearward in the absorbent article 1. The size and shape of the absorbent layers may be different from those shown in the figures without departing from the object of the present disclosure. Moreover, the second absorbent layer 15 may be omitted in the absorbent article 1 according to the embodiment or the article 1 may comprise one or more further absorbent layers.

The first absorbent layer 11 has an opening 12 extending completely through the layer 1. The first absorbent layer 11 may have one or more openings 12 of different shapes and configurations. One elongated opening 12 is however preferred. The longitudinal length of the opening 12 is 10-60% of the longitudinal length of the first absorbent layer 11. The length of the opening may be e.g. about 100 mm. The opening 12 is located with 20-50% of its longitudinal length in the front portion 6 of the first absorbent layer 11. The transverse dimension of the opening 12 is larger in the front portion 6 of the first absorbent layer 11 than the transverse dimension of the opening 12 in the back portion 7 of the first absorbent layer 11. The opening 12 will in use of the article be placed directly beneath the urethra and the vaginal opening of a female wearer. Any body fluid that is released to the absorbent article 1 will directly be collected in the opening 12 and be temporarily contained therein until it is distributed further into and throughout the absorbent core 10.

In FIG. 4 the topsheet 8 does not extend down into the cavity that is defined by the opening 12 in the first absorbent layer 11 and the topsheet-facing surface of the fluid flow control structure 13, but may do so. A portion of the fluid that is collected in the opening 12 may be absorbed by the first absorbent layer through the walls of the first absorbent layer in the opening 12. However, the majority of the fluid will continue downward in the absorbent article 1 and into the fluid flow control structure 13 where it is distributed longitudinally and laterally along the flow control structure 13.

The fluid flow control structure 13 is shown in FIGS. 1-5 to be of rectangular shape and to be surrounded in the longitudinal and lateral directions by portions of the absorbent layers 11, 15. It is generally advantageous if the fluid flow control structure 13 has smaller width and also is shorter than the absorbent layers 11, 15.

The fluid flow control structure 13 may be a three-layer structure consisting of a non-perforated fibrous polymeric layer that is sandwiched between a first perforated polymeric layer and a second perforated polymeric layer.

The components in the absorbent article 1 may be connected to each other by conventional means such as construction adhesive, heat bonding, ultrasonic bonding, etc. It may not be necessary to bond internal components of the incontinence protector to each other by special bonding means. Hence, it may suffice that such components are held together by frictional forces.

Figure 6:
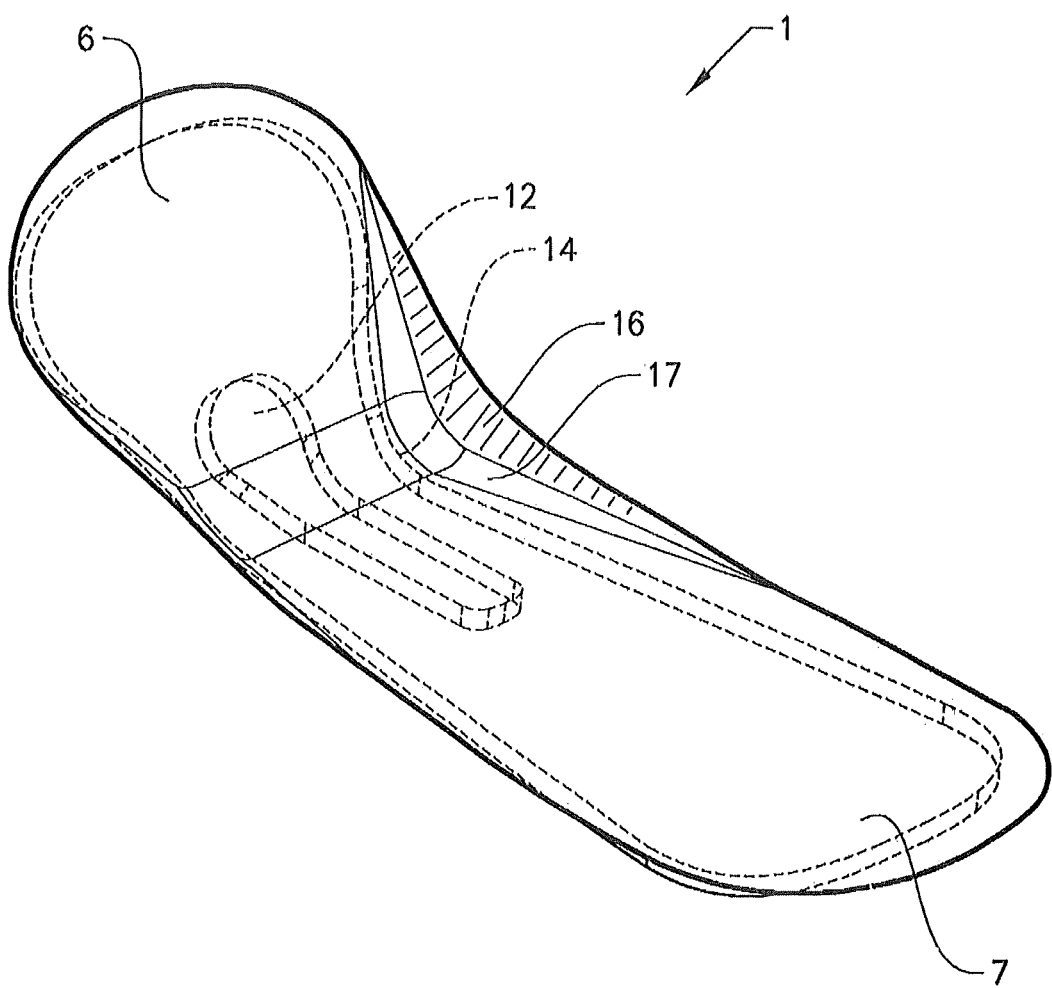
FIG. 6 is a side elevation view of an embodiment of an absorbent article according to an embodiment.

FIG. 6 is a side elevation view of an exemplary embodiment of the article 1 according to the embodiment. The narrow transversal transition 14 between the front 6 and back 7 portion of the first absorbent layer (11) and the asymmetric shape of the layer provides an improved fit of the article on the wearer and which is further enhanced by the interspace 17 and the elastic members 16.

The invention claimed is:

1. An absorbent article comprising longitudinal side edges, transversal end edges, a fluid permeable topsheet, a fluid impermeable backsheet, and an absorbent core located between the topsheet and the backsheet, the absorbent core comprising a first absorbent layer having a longitudinal front portion and a longitudinal back portion, the first absorbent layer having an opening extending therethrough and 20-50% of the longitudinal length of the opening located in the front portion of the first absorbent layer, a fluid flow control structure being located between the first absorbent layer and the backsheet, a second absorbent layer located between the fluid flow control structure and the backsheet, the second absorbent layer having a smaller surface area than the first absorbent layer, and an elastic member being arranged along each longitudinal side edge of the absorbent article, wherein
a narrow transversal transition is located between the front portion and the back portion of the first absorbent layer, the width of the narrow transversal transition is 50-75% of the widest transversal width of the front portion of the first absorbent layer, the front portion of the first absorbent layer constitutes 20-40% of the total longitudinal length of the first absorbent layer, and an interspace is located in an area between the elastic member and the first absorbent layer at least in an area laterally outside the narrow transversal transition.

2. Absorbent article according to claim 1, wherein the interspace has a maximum lateral extension between an inner side edge of the elastic member and a proximal side edge of the first absorbent layer of at least 15 mm and less than 40 mm.

3. Absorbent article according to claim 1, wherein the elastic member is arranged along each longitudinal side edge of the sanitary napkin, at least laterally outside the narrow transversal transition between the front portion and the back portion of the first absorbent layer.

4. Absorbent article according to claim 1, wherein the longitudinal extension of the opening and the elastic member in the back portion of the first absorbent layer is 20-50%.

5. Absorbent article according to claim 1, wherein the maximal longitudinal extension of the elastic member in the back portion of the first absorbent layer is the same as the longitudinal extension of the opening.

6. Absorbent article according to claim 1, wherein the absorbent article has a scoop shape.

7. Absorbent article according to claim 1, wherein the elastic member is sandwiched between the topsheet and the backsheet.

8. Absorbent article according to claim 1, wherein the longitudinal length of the opening in the first absorbent layer is 20-40% of the longitudinal length of the first absorbent layer.

9. Absorbent article according to claim 1, wherein the width of the narrow transversal transition is 50-75% of the widest transversal width of the back portion of the first absorbent layer.

10. Absorbent article according to claim 1, wherein the width of the narrow transversal transition is 55-70% of the widest transversal width of the front portion of the first absorbent layer.

11. Absorbent article according to claim 1, wherein the longitudinal extension of the narrow transversal transition is 5-20% of the longitudinal length of the first absorbent layer.

12. Absorbent article according to claim 1, wherein the topsheet and the backsheet extend together laterally outside of the first absorbent layer.

13. Absorbent article according to claim 1, wherein the transverse dimension of the opening is larger in the front portion of the first absorbent layer than the transverse dimension of the opening in the back portion of the first absorbent layer.

14. Absorbent article according to claim 1, wherein each longitudinal side edge is an outermost edge of the absorbent article, and each elastic member is provided at the outermost edge.

15. Absorbent article according to claim 1, wherein the interspace extends along the elastic member so that the elastic member does not overlap the first absorbent layer.

16. Absorbent article according to claim 1, wherein the elastic member is attached to the topsheet along each longitudinal side edge of the absorbent article.

* * * * *